(12) United States Patent
Li et al.

(10) Patent No.: US 11,348,243 B2
(45) Date of Patent: May 31, 2022

(54) SYSTEMS AND METHODS FOR MEDICAL IMAGE STYLE TRANSFER USING DEEP NEURAL NETWORKS

(71) Applicant: GE Precision Healthcare LLC, Milwaukee, WI (US)

(72) Inventors: Zhijin Li, Paris (FR); Serge Muller, Oconomowoc, WI (US); Giovanni Palma, Chaville (FR); Razvan Iordache, Paris (FR)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/752,461

(22) Filed: Jan. 24, 2020

(65) Prior Publication Data
US 2021/0233239 A1  Jul. 29, 2021

(51) Int. Cl.
  *G06K 9/00* (2022.01)
  *G06T 7/00* (2017.01)
  *G16H 30/40* (2018.01)

(52) U.S. Cl.
  CPC ........... *G06T 7/0014* (2013.01); *G16H 30/40* (2018.01); *G06T 2207/20081* (2013.01); *G06T 2207/20084* (2013.01); *G06T 2207/30096* (2013.01); *G06T 2207/30168* (2013.01)

(58) Field of Classification Search
  CPC ......... G06T 7/0014; G06T 2207/20081; G06T 2207/20084; G06T 2207/30096; G06T 2207/30168; G16H 30/40
  See application file for complete search history.

(56) References Cited

U.S. PATENT DOCUMENTS

| | | |
|---|---|---|
| 6,891,920 B1 | 5/2005 | Minyard et al. |
| 8,235,726 B2 | 8/2012 | Hoostettler et al. |
| 8,241,041 B2 | 8/2012 | Hostettler et al. |
| 8,290,251 B2 | 8/2012 | Mahajan et al. |

(Continued)

OTHER PUBLICATIONS

Carton, A. et al., "Development and validation of a simulation procedure to study the visibility of micro calcifications in digital mammograms," Medical Physics, vol. 30, No. 8, Aug. 2003, 8 pages.

(Continued)

*Primary Examiner* — Atiba O Fitzpatrick
(74) *Attorney, Agent, or Firm* — Fletcher Yoder, P.C.

(57) ABSTRACT

The current disclosure provides for mapping medical images to style transferred medical images using deep neural networks, while maintaining clinical quality of the style transferred medical image, thereby enabling a clinician to evaluate medical images in a preferred style without loss of clinically relevant content. In one embodiment the current disclosure provides for a method comprising, acquiring a medical image of an anatomical region of a subject, wherein the medical image is in a first style, selecting a target style, wherein the target style is distinct from the first style, selecting a clinical quality metric, selecting a trained style transfer network based on the target style and the clinical quality metric, mapping the medical image to a style transferred medical image using the trained style transfer network, wherein the style transferred medical image is in the target style, and displaying the style transferred medical image via a display device.

20 Claims, 5 Drawing Sheets

(56) References Cited

U.S. PATENT DOCUMENTS

| | | | |
|---|---|---|---|
| 8,761,471 | B2 | 6/2014 | Ozawa et al. |
| 8,965,484 | B2 | 2/2015 | Quelever et al. |
| 9,384,546 | B2 | 7/2016 | Zheng et al. |
| 9,582,916 | B2 | 2/2017 | Vemulapalli et al. |
| 9,595,120 | B2 | 3/2017 | Nguyen et al. |
| 9,760,807 | B2 | 9/2017 | Zhou et al. |
| 9,824,302 | B2 | 11/2017 | Grbic et al. |
| 9,892,361 | B2 | 2/2018 | Nguyen et al. |
| 9,922,272 | B2 | 3/2018 | Cheng et al. |
| 9,971,958 | B2 | 5/2018 | Liu et al. |
| 10,043,088 | B2 | 8/2018 | Odry et al. |
| 10,062,014 | B2 | 8/2018 | Zhou et al. |
| 10,074,038 | B2 | 9/2018 | Hsieh et al. |
| 10,096,109 | B1 | 10/2018 | Zaharchuk et al. |
| 10,102,451 | B2 | 10/2018 | Han |
| 2008/0025583 | A1 | 1/2008 | Jabri et al. |
| 2008/0037851 | A1 | 2/2008 | Takayama |
| 2008/0312884 | A1 | 12/2008 | Hostettler et al. |
| 2009/0238421 | A1 | 9/2009 | Zhang et al. |
| 2010/0046829 | A1 | 2/2010 | Mahajan et al. |
| 2016/0133037 | A1 | 5/2016 | Vemulapalli et al. |
| 2017/0372193 | A1 | 12/2017 | Mailhe et al. |
| 2018/0042564 | A1 | 2/2018 | Zhou |
| 2018/0225823 | A1 | 8/2018 | Zhou et al. |
| 2018/0314716 | A1 | 11/2018 | Kim et al. |
| 2018/0374245 | A1* | 12/2018 | Xu .................. A61B 6/5282 |
| 2019/0318474 | A1* | 10/2019 | Han .................. G06K 9/6267 |
| 2019/0362522 | A1* | 11/2019 | Han .................. A61B 5/7267 |
| 2020/0327662 | A1* | 10/2020 | Liu .................. G16H 30/40 |
| 2020/0372301 | A1* | 11/2020 | Kearney .............. A61B 6/469 |
| 2021/0063518 | A1* | 3/2021 | Zhang ............... G06K 9/46 |

OTHER PUBLICATIONS

Carton, A. et al., "Quantification of Al-equivalent thickness of just visible microcalcifications in full field digital mammograms," Medical Physics, vol. 31, No. 7, Jul. 2004, 14 pages.

Shaheen, E. et al., "The simulation of 3D microcalcification clusters in 2D digital mammography and breast tomosynthesis," Medical Physics, vol. 38, No. 12, Dec. 2011, 13 pages.

Mackenzie, A. et al., "Conversion of mammographic images to appear with the noise and sharpness characteristics of a different detector and x-ray system," Medical Physics, vol. 39, No. 5, May 2012, 15 pages.

Mackenzie, A. et al., "Converting One Set of Mammograms to Simulate a Range of Detector Imaging Characteristics for Observer Studies," Proceedings of the 11th International Workshop on Digital Mammography (IWDM 2012), Jul. 8, 2012, Philadelphia, Pennsylvania, 8 pages.

Mackenzie, A. et al., "Characterisation of a breast tomosynthesis unit to simulate images," Proceedings SPIE—The International Society of Optical Engineering, vol. 8668, Medical Imaging 2013: Physics of Medical Imaging, Apr. 4, 2013, 8 pages.

Mackenzie, A. et al., "Image simulation and a model of noise power spectra across a range of mammographic beam qualities," Medical Physics, vol. 41, No. 12, Dec. 2014, 15 pages.

Han, S. et al., "A Preliminary Study of an Image Synthesis Method to Simulate the Change in the incident X-ray spectrum by Using Thickness Information," Journal of the Korean Physical Society, vol. 68, No. 6, Mar. 2016, 6 pages.

Borges, L. et al., "Simulation of Dose Reduction in Digital Breast Tomosynthesis," Proceedings of the 13th International Workshop on Breast Imaging (IWDM 2016), Jun. 19, 2016, Malmö, Sweden, 8 pages.

Borges, L. et al., "Method for simulating dose reduction in digital mammography using the Anscombe transformation," Medical Physics, vol. 43, No. 6, Jun. 2016, 11 pages.

Borges, L. et al., "Method for Simulating Dose Reduction in Digital Breast Tomosynthesis," IEEE Transactions on Medical Imaging, vol. 36, No. 11, Nov. 2017, Available Online Jun. 15, 2017, 13 pages.

Boita, J. et al., "Breast phantom validation of a mammographic image modification method," Proceedings of the Fourteenth International Workshop on Breast Imaging (IWBI 2018), Jul. 6, 2018, Atlanta, Georgia, 8 pages.

* cited by examiner

SYSTEMS AND METHODS FOR MEDICAL IMAGE STYLE TRANSFER USING DEEP NEURAL NETWORKS

TECHNICAL FIELD

Embodiments of the subject matter disclosed herein relate to medical imaging, and more particularly, to systems and methods for mapping medical images to a target style domain using deep neural networks.

BACKGROUND

Image processing devices are often used to obtain internal physiological information of a subject, such as a patient. For example, an image processing device may be used to obtain images of the bone structure, the brain, the heart, the lungs, and various other anatomical regions of a patient. Image processing devices may include magnetic resonance imaging (MRI) systems, computed tomography (CT) systems, positron emission tomography (PET) systems, PET/MR systems, x-ray systems, ultrasound systems, C-arm systems, and various other imaging modalities.

Medical images from different imaging modalities (e.g., MRI images versus CT images) and medical images from the same imaging modality but from different imaging systems (e.g., MRI images from two different MRI systems produced by two different manufactures, or two different models of MRI systems produced by a same manufacturer), may possess distinct appearance characteristics attributed to acquisition parameters and manufacturer-specific image-processing algorithms. In screening and diagnostic image review, clinicians often need to adapt to modality and manufacturer-specific image appearance characteristics, as medical images for a patient may be acquired using multiple imaging modalities or using multiple imaging systems of different models or from different manufacturers. Clinicians may have appearance preferences for medical images, for example, a clinician may have a greater degree of experience diagnosing medical images in a first style (that is, medical images with a first set of appearance characteristics), and may therefore prefer to evaluate/diagnose medical images in the first style. Presentation of medical images from different imaging modalities/manufacturers/models, which comprise appearance characteristics which do not match with a clinician's preferences, may require additional efforts for a clinician to adopt to the different appearance characteristics, therefore hinder a clinician's review and diagnostic efficiency. Similarly, deep neural networks and other machine learning models trained to evaluate medical images of a first style may perform poorly (e.g., with reduced accuracy) when evaluating medical images in styles distinct from the first style (that is, medical images with appearance characteristics different from those of the first style).

Some previous approaches to address the above identified issues attempt to match physical parameters of an originating image processing device and a target image processing device (the image processing device producing images matching a clinician's appearance characteristic preferences), requiring knowledge of the physical parameters and settings of both systems, which may, in some examples, require laboratory testing of both the originating medical imaging device and the target medical imaging device. Acquisition of the physical parameters of image processing devices may require substantial time, and may need to be repeated for each distinct imaging system and imaging modality. Thus, the above approach may not scale efficiently to larger numbers of image processing devices, and may be impractical in terms of implementation time and expense. Other approaches based on conventional image feature analysis or supervised machine learning may require datasets comprising extensive, manually selected corresponding pairs of images of the same anatomical region (e.g., a first medical image of the anatomical region in an originating style, and a second medical image of the anatomical region in a target style). However, the acquisition of such pair datasets is often challenging in practice. Additionally, current attempts to map medical images from an originating style to a target style do not explicitly control the clinical image quality during the mapping process, thus may incur substantial clinical quality degradation (e.g., a morphology of a tumor is altered upon adjusting image appearance characteristics to match a designated target style, thereby reducing a clinician's ability to detect the presence of the tumor in the style transferred image).

Therefore, based on the above issues and limitations, it is generally desirable to explore techniques for transferring style of medical images, without requiring knowledge of the physical parameters of the originating or target image processing devices, without requiring manual selections of paired images with the same anatomical region, while preserving the clinical quality of the medical images.

SUMMARY

The current disclosure at least partially addresses one or more of the above identified issues. In one embodiment, the current disclosure provides a method for transferring style of a medical image to a target style, while maintaining the anatomical content of the medical image, as well as the clinical/diagnostic quality of the medical image, comprising, acquiring a medical image of an anatomical region of a subject, wherein the medical image is in a first style, selecting a target style, wherein the target style is distinct from the first style, selecting a clinical quality metric, selecting a trained style transfer network based on the target style and the clinical quality metric, mapping the medical image to a style transferred medical image using the trained style transfer network, wherein the style transferred medical image is in the target style, and displaying the style transferred medical image via a display device. The first style and the target style of the medical image are implicitly characterized by the corresponding un-paired datasets of acquired medical images with the first style and acquired medical images with the target style and are automatically learned by the style transfer network during an unsupervised training process. In this way, one or more appearance characteristics of a medical image may be mapped to one or more target appearance characteristics (also referred to herein as a target style), with neither measurement of the physical parameters of a target or originating image processing device, nor manual selection of paired images. Further, by selecting a trained style transfer network based on a clinical quality metric, the clinical quality of the medical image with respect to one or more clinical qualities being evaluated by a clinician or downstream image processing system, may be better preserved in the style transferred medical image.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
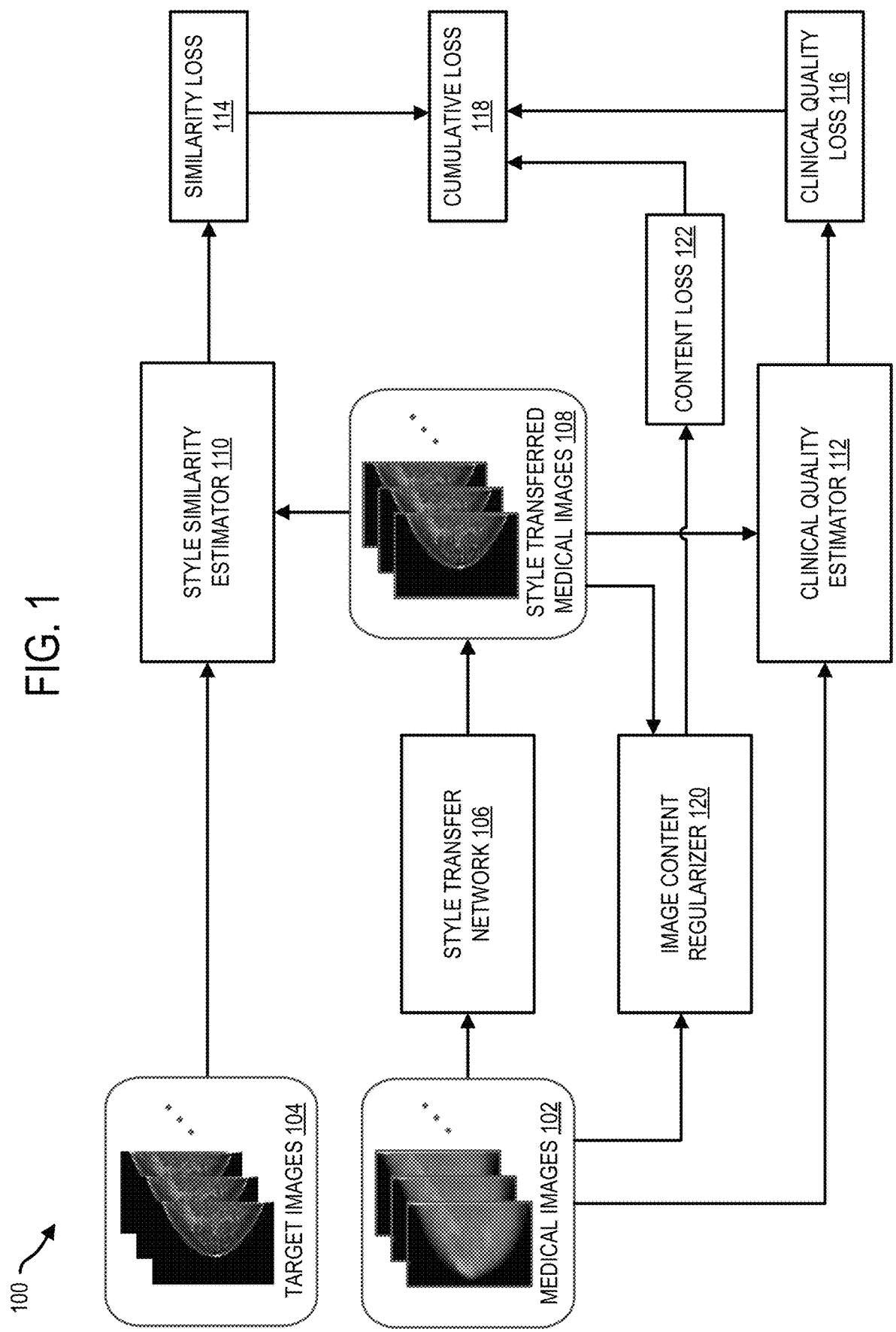
FIG. 1 shows a block diagram of an exemplary embodiment of a style transfer network training system.

The drawings illustrate specific aspects of the described systems and methods for mapping one or more medical images in a first style to one or more corresponding medical images in a target style using deep neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to systems and methods for mapping medical images from a first style, to a target style, while preserving clinical/diagnostic quality of the medical images, using one or more deep neural networks. As an example, breast images from different imaging modalities and manufacturers present their unique appearance characteristics attributed to acquisition specification and manufacturer-specific image-processing algorithms. In screening and diagnostic image review, clinicians often need to adapt to modality- and manufacturer-specific image appearance characteristics for optimized review efficiency. Potentially, clinicians' efficiency can be hindered when modality and/or manufacturer changes, or when available review settings cannot meet clinicians' preference for the optimal review. Thus, to increase clinical review efficiency, an appearance transfer algorithm can be used, offering a transition between original image appearance and a target image appearance that the clinicians are adapted to. Existing transfer algorithms are either based on matching physical parameters of original and target imaging systems, requiring prior knowledge of physical parameters and laboratory measurements on both systems, or based on matching image-to-image characteristics, requiring selection of a specific target image to pair-up with the original image. Also, quantitative metrics are currently unavailable to increase a probability that the style transfer does not hinder task-based clinical image quality, such as lesion detectability.

Further, to avoid manual selection of target images and physical measurements on imaging systems, which may be prohibitively time consuming and/or expensive, an appearance transfer algorithm directly trainable from unpaired and unlabeled images is desired. Additionally, it may be desirable to incorporate constraints on task-based clinical image quality of transferred images, to reduce a probability of clinical quality degradation from the style transfer process.

The current disclosure provides systems and methods for transformation of an original image, having an original appearance, to a style transferred medical image, having target set of appearance characteristics (wherein the target set of appearance characteristics may herein be referred to as a target style). In one embodiment, the original image may be transformed to the target style using a trained style transfer network. The current disclosure further provides for training systems and methods, enabling a style transfer network to be trained in an unsupervised fashion to learn a mapping from a first style to a target style. The training systems and methods disclosed herein do not require measurement of physical characteristics of image processing devices, nor do the training systems and methods require manually labeled images, or pairs of images. Further, the training systems and methods disclosed herein include constraints on clinical quality, which may reduce a probability of clinical quality degradation in style transferred medical images.

Figure 2:
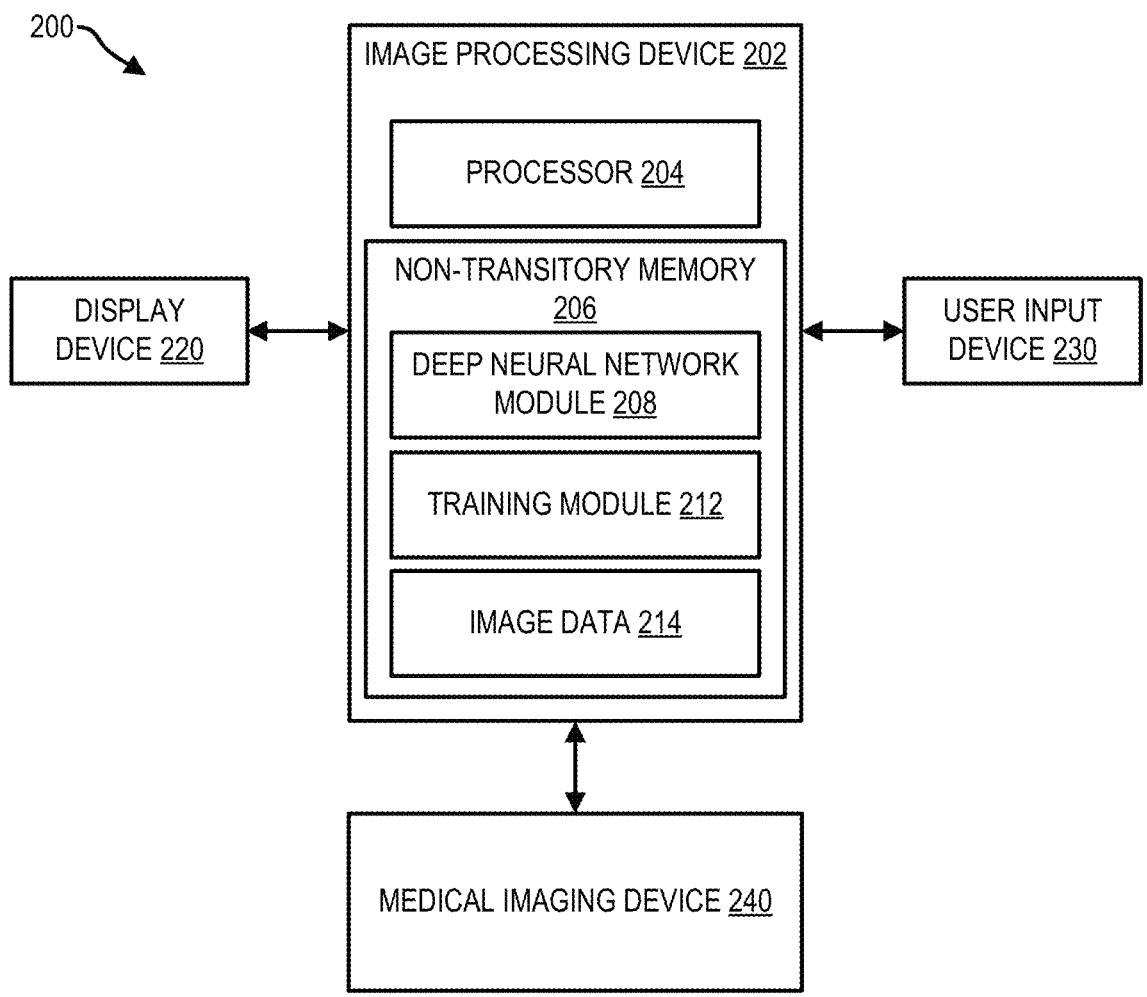
FIG. 2 shows a block diagram of an exemplary embodiment of an image processing system configured to map medical images from an originating style to a target style, using a trained style transfer network.
Figure 4:
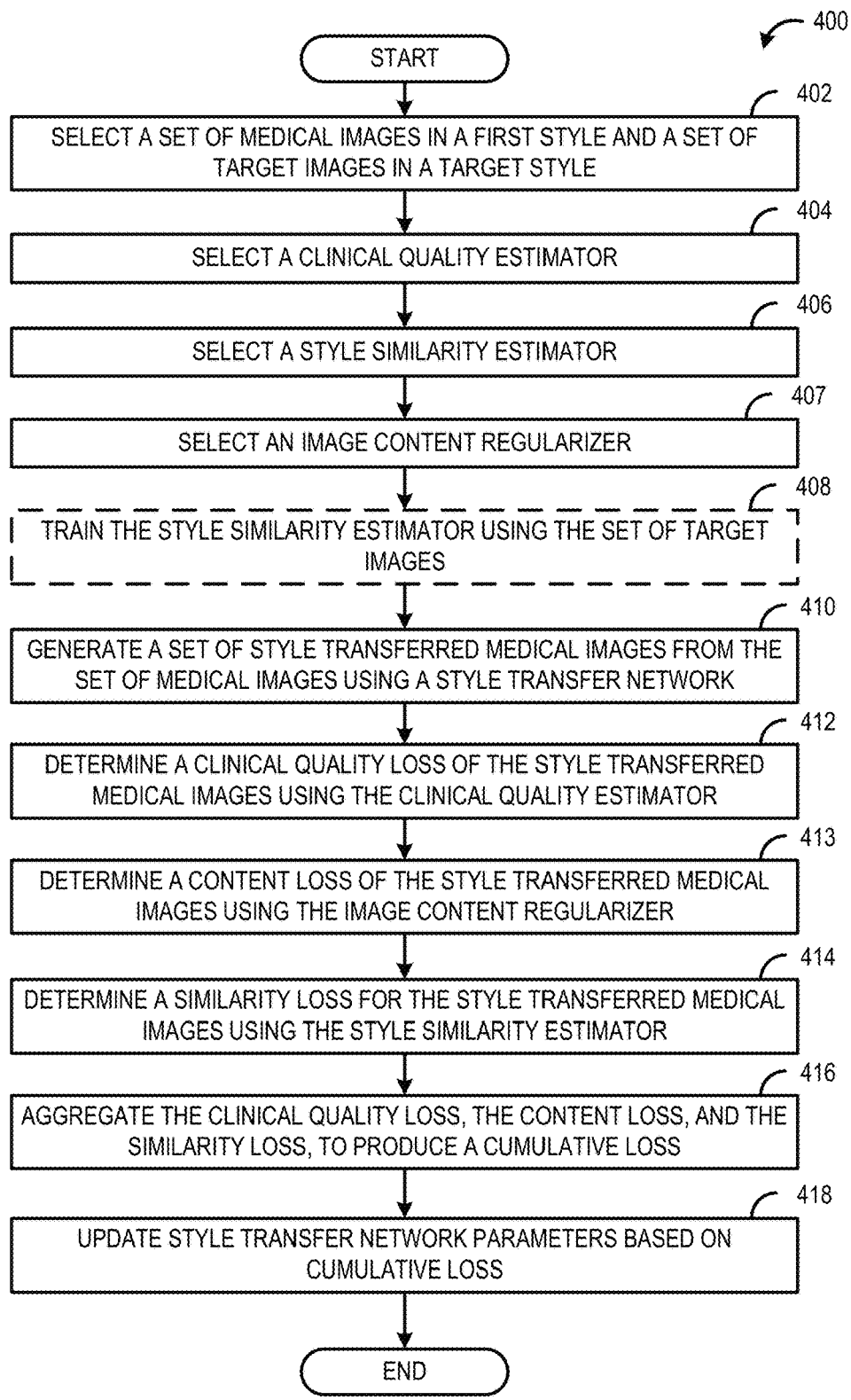
FIG. 4 shows a flowchart of an exemplary method for training a style transfer network using the style transfer network training system of FIG. 1.

In one embodiment, an image processing device, such as image processing device 202, shown in FIG. 2, may train a style transfer network 106 using a style transfer network training system 100, shown in FIG. 1 by executing one or more operations of method 400, shown in FIG. 4. Method 400 comprises training the style transfer network 106 to learn a mapping from a first style domain to a target style domain, by adjusting parameters to reduce a cumulative loss. The cumulative loss comprises a similarity loss 114, which may be determined based on output from the style similarity estimator 110, a content loss 122, which may be determined by an image content regularizer 120, and a clinical quality loss 116, which may be determined based on output from a clinical quality estimator 112. The clinical quality loss 116 helps ensure one or more aspects of clinical quality is maintained through the mapping from the first style to the target style by imposing a penalty on the style transfer network 106 based on changes in clinical quality between input medical images 102 in the first style, and the corresponding style transferred medical images 108 in the target style.

Figure 3:
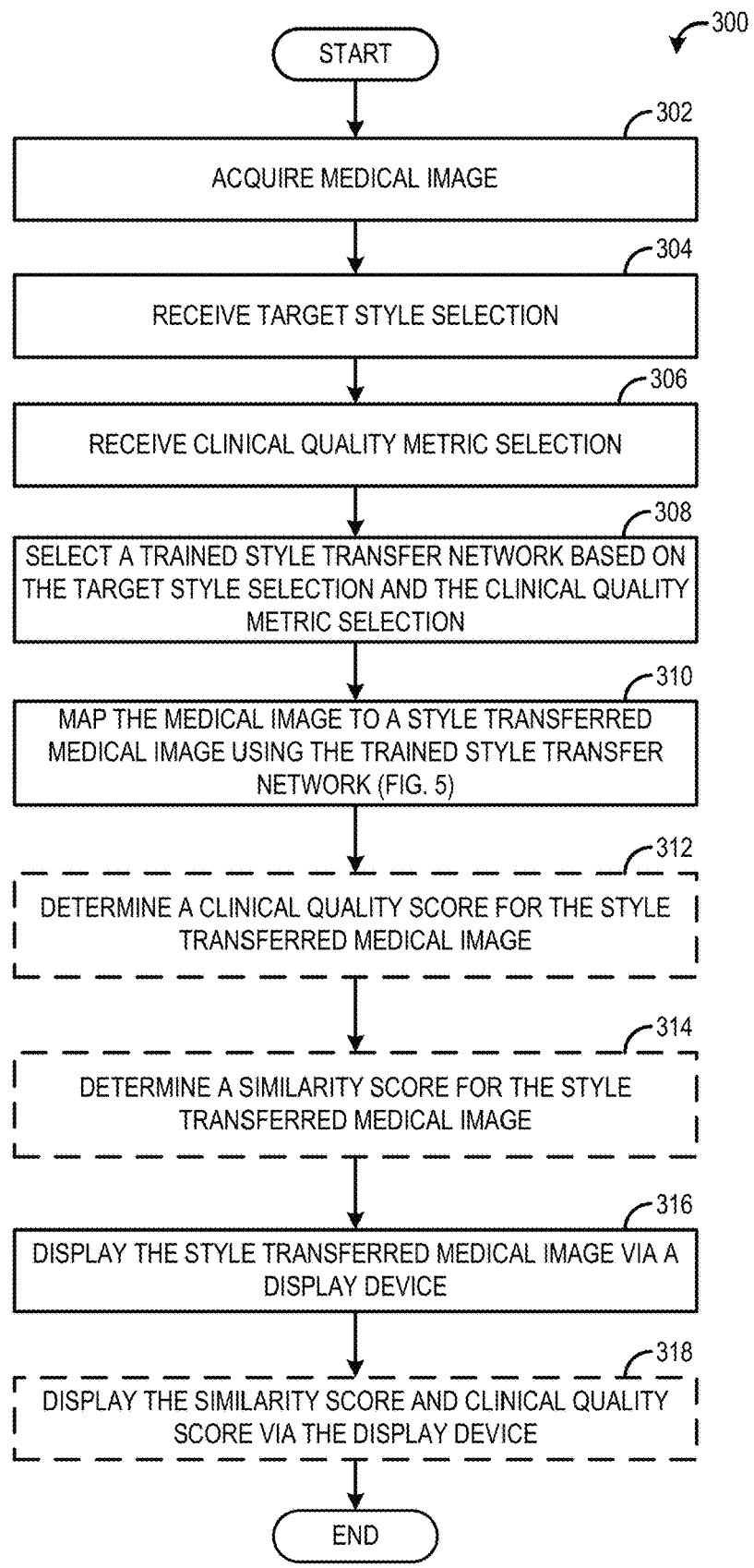
FIG. 3 shows a flowchart of an exemplary method for mapping one or more medical images from a first style to a target style, using a trained style transfer network.
Figure 5:
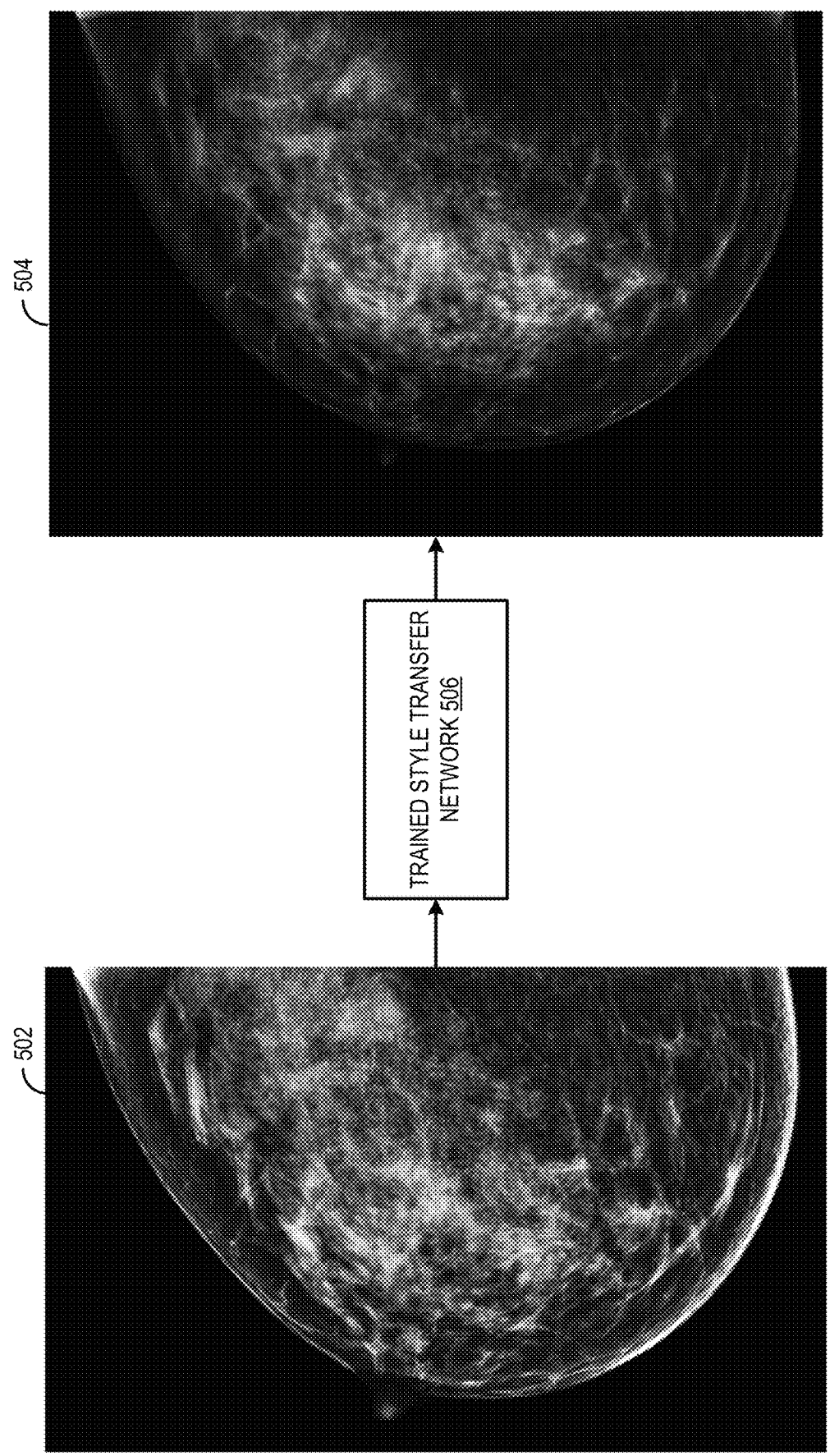
FIG. 5 shows an example of a first medical image and a corresponding style transferred medical image produced by a trained style transfer network.

Trained style transfer networks may be implemented by an image processing device, such as image processing device 202, to map one or more medical images from the first style to one or more corresponding style transferred medical images, in the target style, by executing one or more operations of method 300, shown in FIG. 3. One example of an input medical image in a first style, and a corresponding style transferred medical image, in a target style, which may be produced by a trained style transfer network, is shown in FIG. 5.

Referring to FIG. 1, an example of a style transfer network training system 100 is shown. Style transfer network training system 100 may be implemented by one or more computing systems, such as image processing device 202, shown in FIG. 2, to train a style transfer network to learn a mapping from a first style domain to a target style domain. Style transfer network training system 100 comprises a style transfer network 106 (to be trained), a style similarity estimator 110, a clinical quality estimator 112, and an image content regularizer 120. The style similarity estimator 110, the clinical quality estimator 112, and the image content regularizer 120, determine a similarity loss 114, a clinical quality loss 116, and a content loss 122, respectively, which are aggregated to form a cumulative loss 118. The parameters of style transfer network 106 are then iteratively updated based on the cumulative loss 118 during the training process.

Style transfer network training system 100 receives as input one or more target images 104, and one or more medical images 102, wherein the target images 104 differ in at least one appearance characteristic with respect to medical images 102. In some embodiments, appearance characteristics (herein also referred to as visual characteristics) comprise features such as, but not limited to brightness, color, contrast, shading, texture, sharpness and noise level etc.

The number of target images 104 and the number of medical images 102 may be different or equal, but need not necessarily belong to a same patient, or include a same anatomical region. Further, the target images 104 and the medical images 102 are not paired or labeled, such as in conventional supervised training. The target images 104 and medical images 102 may comprise medical images from different patients, may comprise different anatomical regions, may be different in number, and may be unlabeled. In particular, the appearance characteristics of target images 104 and medical images 102 need not be explicitly identified or labeled, as the style similarity estimator 110 may be configured to automatically identify and extract appearance characteristics from input images. By bypassing the need for labeled training data, style transfer network training system 100 greatly increases the scalability and efficiency of training style transfer networks for a plurality of different style transfer mappings, as the amount of usable data is greatly increased, while the amount of pre-processing of the training data is greatly reduced.

In some embodiments, medical images 102 may be from a first imaging modality and/or a first imaging system, while target images 104 may be from a second imaging modality and/or a second imaging system. In some embodiments, target images 104 may comprise medical images having one or more manually adjusted appearance characteristics, wherein the manually adjusted appearance characteristics may be set by a clinician, to suit the clinician's preferences. As an example, a clinician may prefer particular brightness and contrast settings, and may manually adjust the brightness and contrast of one or more medical images to meet these preferences. These manually brightness and contrast adjusted images may be fed to style transfer training system 100 as target images 104, and a style transfer network 106 may be trained to automatically map appearance characteristics of acquired medical images to the clinician preferred appearance characteristics of target images 104.

Style transfer network training system 100 may be implemented according to one or more operations of method 400, to train a style transfer network to learn a mapping from the style domain characterized by medical images 102, to the style domain characterized by target images 104. Style transfer network 106 is configured to receive data from medical images 102, and to map this data to corresponding style transferred medical images 108. In some embodiments, style transfer network 106 comprises a parametric generative transfer model. In some embodiments, style transfer network 106 may comprise a deep neural network. In some embodiments, style transfer network 106 may comprise a deep neural network having a U-net architecture. In some embodiments, style transfer network 106 may comprise a deep neural network having a variational autoencoder architecture, comprising a first encoding portion, which compresses the information of medical images 102 into a condensed representation/encoding, and a decoder portion, which decompresses the condensed representation/encoding to a variation of the medical images 102. In some embodiments, the encoding portion comprises one or more convolutional layers, which in turn comprise one or more convolutional filters. The convolutional filters may comprise a plurality of weights, wherein the values of the weights are learned during a training procedure, such as the training method of FIG. 4. The convolutional filters may correspond to one or more visual features/patterns, thereby enabling the style transfer network 106 to identify and extract visual features from input medical images 102. The encoding portion may further comprise one or more down sampling operations, and/or one or more activation functions. The decoding portion may comprise one or more up-sampling, and/or deconvolution operations, which enable a compressed representation of the medical images 102 to be reconstructed into an image of the same size as the input medical images 102.

Output of style transfer network 106 may be used to generate style transferred medical images 108. In some embodiments, style transfer network 106 may directly output style transferred medical images 108. Style transferred medical images 108 may comprise a same number of images as medical images 102, wherein for each image of medical images 102, a corresponding style transferred medical image is produced, such that there is a 1-to-1 correspondence between medical images 102 and style transferred medical images 108. Style transferred medical images 108, along with medical images 102 and/or target images 104 may be fed to style similarity estimator 110, clinical quality estimator 112, and image content regularizer 120, to determine a similarity loss 114, a clinical quality loss 116, and a content loss 122, respectively. The various losses may be aggregated to form a cumulative loss 118, wherein the cumulative loss 118 may be used to update parameters of style transfer network 106, such as is described in method 400 of FIG. 4.

The style transferred medical images 108, along with target images 104, may be fed to style similarity estimator 110, for determination of a similarity loss 114. The similarity loss 114 represents a quantification of the differences in appearance between style transferred medical images 108 and target images 104. In other words, style similarity estimator 110 evaluates the visual characteristics of style transferred medical images 108, and compares this with the visual characteristics of target images 104, to produce a numerical value indicating a degree of stylistic similarity/difference between target images 104 and style transferred medical images 108.

Style similarity estimator 110 may comprise one or more differentiable functions, configured to receive style transferred medical images 108 and target images 104 as input, and output a similarity score/similarity loss 114, indicating the similarity in appearance between the style transferred medical images 108 and the target images 104. In some embodiments, style similarity estimator 110 is configured to output a probability of an input image belonging to the set of target images 104. In one embodiment, style similarity estimator 110 may comprise a discriminator network. The discriminator network may be trained to output the probability that an input image belongs to the target images 104. Similarity loss 114 may increase in response to increased accuracy of the discriminator network correctly distinguishing between target images 104 and style transferred medical images 108. Similarity loss 114 may decrease in response to decreased accuracy (e.g., an accuracy of 0.5 indicates the accuracy of a random guess, whereas an accuracy of 1.0 indicates the discriminator is able to distinguish target images from style transferred images with 100% accuracy) of the discriminator network correctly distinguishing between target images 104 and style transferred medical images 108. The parameters of style transfer network 106 may be adjusted to reduce the similarity loss 114, which has the effect of increasing the visual similarity of style transferred medical images 108 to target images 104.

Similarly, the clinical quality estimator 112 may receive both medical images 102, and style transferred medical images 108, and determine a clinical quality loss 116 based thereon. The clinical quality loss 116 represents a difference in clinical quality for one or more clinical quality metrics, between medical images 102 and style transferred medical images 108. In some embodiments, clinical quality estimator 112 may comprise a deep convolutional neural network, trained to identify one or more clinically relevant features in an input image, and to produce a score indicating one or more attributes of the identified clinically relevant feature. In some embodiments, clinical quality estimator 112 comprises a deep neural network pre-trained to produce a cancer classification score for input medical images, and clinical quality loss 116 may increase as the difference in cancer score between medical images 102 and style transferred medical images 108 increases. In some embodiments, clinical quality estimator 112 comprises a model observer producing a lesion detectability index for input medical images, and clinical quality loss 116 may increase as the difference in lesion detectability between medical images 102 and style transferred medical images 108 increases. In other words, clinical quality estimator 112 forces style transfer network 106 to maintain one or more clinical quality metrics of style transferred medical images 108 within a threshold difference of the clinical quality metrics of medical images 102.

Style transfer network training system 100 further comprises image content regularizer 120. Image content regularizer may comprise one or more differentiable functions, which take medical images 102 and style transferred medical images 108 as input, and produce content loss 122 as output. Image content regularizer 120 may be configured such that as the difference in anatomical content between an input medical image, and an output style transferred image increases, the content loss 122 also increases. Image content regularizer may be configured to compute pixelwise distances between medical images 102 and style transferred medical images 108, wherein content loss 122 may be based on the summed or averaged pixelwise distances. The distance metric used in the image content regularizer may be, but are not limited to the L1 or the L2 distance. Image content regularizer 120 helps tether the overall content, as opposed to the style, of style transferred medical images 108, to the content of medical images 102. In other words, by introducing a content loss 122, produced by image content regularizer 120, into the cumulative loss 118, and by training style transfer network 106 to minimize the cumulative loss 118, style transfer network 106 may produce style transferred medical images 108 which preserve the anatomical content of medical images 102.

The similarity loss 114, the content loss 122, and the clinical quality loss 116, may be aggregated to form a cumulative loss 118, wherein the cumulative loss 118 may comprise a weighted sum or weighted average of the similarity loss 114, the content loss 122, and the clinical quality loss 116. In some embodiments, each of the similarity loss 114, the content loss 122, and the clinical quality loss 116, may have an associated weight (that is, three distinct weights may be used to determine the cumulative loss 118, one for each of the above said loss terms), and the cumulative loss 118 may be determined by multiplying each of similarity loss 114, the content loss 122, and the clinical quality loss 116 by its associated weight, and summing the products so obtained.

The weighting of each of the loss terms during determination of the cumulative loss 118 serves to provide flexibility in the relative importance of each type of loss in the training process of style transfer network 106, thereby enabling style transfer network 106 to learn a user customizable style transfer mapping, wherein a relative importance of anatomical content conservation, clinical quality conservation, and target style similarity, are adjustable for training. As an example, setting a weight given to similarity loss 114 to a significantly larger value than the weights for content loss 122, and clinical quality loss 116, may cause style transfer network 106 to learn a mapping which favors similarity between the target images 104 and the style transferred images 108, at the expense of clinical quality conservation and content conservation. Conversely, giving a relatively large weight to clinical quality loss ensures that clinical quality is maintained between the medical images 102 and the style transferred images 108, whereas the visual similarity between the style transferred images 108 and the target images 104 may increase. In some embodiments, the weights used to determine cumulative loss 118 may be manually set. In some embodiments, the weights used to determine cumulative loss 118 may be learned via automatic hyper-parameter search. In one embodiment, the weights used to determine the cumulative loss 118 may be determined using Bayesian optimization or reinforcement learning.

In this way, style transfer network training system 100 enables a style transfer network 106 to learn a map from a first style domain, to a target style domain, while reducing changes in clinical quality or overall anatomical content which may otherwise result from the mapping. Further, by utilizing the style similarity network 110 to automatically identify visual features from both target images 104, and style transferred medical images 108, a similarity loss reflective of a humanly intuitive visual similarity may be obtained, without reliance on use of manually labeled training data sets.

Referring to FIG. 2, a medical imaging system 200 is shown, in accordance with an exemplary embodiment. Medical imaging system 200 comprises image processing device 202, display device 220, user input device 230, and medical imaging device 240. In some embodiments, at least a portion of medical imaging system 200 is disposed at a remote device (e.g., edge device, server, etc.) communicably coupled to the medical imaging system 200 via wired and/or wireless connections. In some embodiments, at least a portion of image processing device 202 is disposed at a separate device (e.g., a workstation) configured to receive images from a storage device which stores images acquired by medical imaging device 240.

Image processing device 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store deep neural network module 208, training module 212, and image data 214. Deep neural network module 208 may include one or more deep neural networks, comprising a plurality of weights and biases, activation functions, loss functions, and instructions for implementing the one or more deep neural networks to map medical images of a first style to corresponding medical images in a target style. For example, deep neural network module 208 may store instructions for implementing one or more neural networks, according to one more steps of method 300, discussed in more detail below. Deep neural network module 208 may include trained and/or untrained neural networks. In some embodiments, the deep neural network module 208 is not disposed at the image processing device 202, but is disposed at a remote device communicably coupled with image processing device 202 via wired or wireless connection. Deep neural network module 208 may include various deep neural network metadata pertaining to the trained and/or untrained networks. In some embodiments, the deep neural network metadata may include an indication of the training data used to train a deep neural network, a training method employed to train a deep neural network, an accuracy/validation score of a deep neural network, and a type clinical quality metric and target style for which the trained deep neural network may be applied.

Non-transitory memory 206 further includes training module 212, which comprises machine executable instructions for training one or more of the deep neural networks stored in deep neural network module 208. In some embodiments, training module 212 may include instructions for implementing a style transfer network training system, such as style transfer network training system 100, shown in FIG. 1. In one embodiment, the training module 212 may include gradient descent algorithms, loss functions, and rules for generating and/or selecting training data for use in training a particular deep neural network. Training module 212 may further include instructions, that when executed by processor 204, cause image processing device 202 to train a style transfer network by executing one or more of the operations of method 400, using target images selected based on a user selected target style, and using a clinical quality estimator selected based on one or more user selected clinical quality metrics, as discussed in more detail with reference to FIG. 4, below. In some embodiments, the training module 212 is not disposed at the image processing device 202, but is disposed remotely, and is communicably coupled with image processing device 202.

Non-transitory memory 206 may further store image data 214, comprising medical imaging data acquired by medical imaging device 240. The medical images stored in image data 214 may comprise medical images from various imaging modalities and/or from various models/manufacturers of medical imaging devices. In some embodiments, medical images stored in image data 214 may include information identifying an imaging modality and/or an imaging device (e.g., model and manufacturer of an imaging device) by which the medical image was acquired. In some embodiments, medical images stored in image data 214 may include regions manually highlighted by clinicians using the user input device 230, wherein the anatomical content of the highlighted region may be prioritized for preservation during the style transfer. In some embodiments, highlighted regions may comprise regions suspected by a clinician to include a lesion/tumor or other pathology. These highlighted regions can be explored by the clinical image quality estimator during training. In some embodiments, image data 214 may comprise MR images captured by an MRI system, CT images captured by a CT imaging system, PET images captured by a PET system, breast images captured by a Mammography system and/or one or more additional types of medical images. In one embodiment, image data 214 may comprise representative target images from a plurality of distinct imaging styles (e.g., different imaging modalities, different image processing algorithms, etc.).

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

Medical imaging system 200 further includes imaging device 240, which may comprise substantially any type of medical imaging device, including MRI, CT, PET, hybrid PET/MR, Mammography, ultrasound, etc. Imaging device 240 may acquire measurement data of an anatomical region of a patient, which may be used to generate medical images. Measurement data, and medical images reconstructed therefrom, may be stored in image data 214, or in other non-transitory storage devices communicably coupled with image processing device 202.

Medical imaging system 200 may further include user input device 230. User input device 230 may comprise one or more of a touchscreen, a keyboard, a mouse, a trackpad, a motion sensing camera, or other device configured to enable a user to interact with and manipulate data within image processing device 202.

Display device 220 may include one or more display devices utilizing virtually any type of technology. In some embodiments, display device 220 may comprise a computer monitor configured to display medical images of various types and styles. Display device 220 may be combined with processor 204, non-transitory memory 206, and/or user input device 230 in a shared enclosure, or may be a peripheral display device and may comprise a monitor, touchscreen, projector, or other display device known in the art, which may enable a user to view medical images reconstructed from measurement data acquired by imaging device 240, and/or interact with various data stored in non-transitory memory 206.

It should be understood that medical imaging system 200 shown in FIG. 2 is for illustration, not for limitation. Another appropriate medical imaging system 200 may include more, fewer, or different components.

Turning to FIG. 3, an example method 300 for mapping medical images having a first set of appearance characteristics (a first style) to anatomically consistent medical images with a different, target set of appearance characteristics (a target style) is shown. Method 300 may be executed by one or more of the systems described above. In one embodiment, image processing device 202 may execute one or more operations of method 300 to map a medical image acquired by imaging device 240 to a clinician selected target style. In this way, a clinician may evaluate/diagnose medical images with a preferred set of appearance characteristics.

Method 300 begins at operation 302, where the medical imaging system acquires a medical image of an anatomical region of a patient. In some embodiments, operation 302 may include medical imaging device 240 acquiring one or more medical images of an anatomical region of interest from a patient. In one example, operation 302 may comprise a medical imaging device acquiring a mammogram image of a patient. Medical images may be acquired using one or more known imaging modalities, including MRI, PET, CT, x-ray, ultrasound, etc. Acquired medical images may comprise two-dimensional (2D) or three-dimensional (3D) images. The acquired medical images may comprise a first set of appearance characteristics, indicative of the imaging modality and/or image reconstruction algorithm and/or image processing algorithms used by the medical imaging device during acquisition and reconstruction/processing of said medical images. The set of appearance characteristics of the acquired medical images may be referred to as a first style, or originating style. In some embodiments, acquired medical images may be transmitted to a remote image processing device. In some embodiments, the medical imaging system includes a built in image processing device.

At operation 304, the image processing device receives a target style selection. The target style selection indicates a preferred set of appearance characteristics. One or more of the appearance characteristics of the preferred set of appearance characteristic may differ from one or more of the appearance characteristics of the acquired medical image. In other words, a style defined by the target style selection may differ from the first style. In some embodiments, operation 304 includes the medical imaging system receiving a target style selection from a user via a user input device. In some embodiments, the image processing device may obtain/retrieve a pre-selected target style selection stored in a location of non-transitory memory wherein a user's preferences are stored. In some embodiments, a target style selection may comprise a designation of a particular imaging modality, which may differ from the imaging modality used to acquire the medical images at operation 302. In some embodiments, the target style selection may comprise a selection of a set of appearance characteristics corresponding to a particular manufacturer or model of an imaging device, wherein the medical imaging system of operation 302 may differ from the particular manufacturer or model of the imaging device of the target style. In some embodiments, the target style selection may comprise a user customized style, comprising one or more user selected appearance characteristics. As an example, a clinician may manually adjust a set of parameters related to image appearance characteristics, including but not limited to contrast, sharpness or other high-level semantic appearance parameters extracted from a neural network such as an autoencoder etc., and may set these preferences as a target style.

At operation 306, the image processing device receives a clinical quality metric selection. In some embodiments, the medical imaging system may receive the clinical quality metric selection from a user via a user input device. In some embodiments, the imaging system may obtain a pre-selected clinical quality metric from a location in non-transitory memory, wherein user preferences are stored. The selected clinical quality metric selection may comprise one or more of lesion detectability, bone fracture detectability, vasculature visualization, etc. In case where clinician highlighted cancer regions, as described in [0037] are available, the clinical quality metric may also comprise a cancer classification score produced by a pre-trained cancer classifier on the highlighted regions. A clinician may select a clinical quality metric relevant to a current task, for example, during screening of medical images for the presence of tumors, a clinician may select (or may have pre-selected) a tumor detectability index/score as the clinical quality metric. In some embodiments, more than one clinical quality metric may be selected at operation 306. In some embodiments, a pre-determined number of clinical quality metrics may be selected in combination.

At operation 308, the image processing device selects a trained style transfer network based on the target style selection and the clinical quality metric selection. Selecting the trained style transfer network based on the selected target style and clinical quality metrics may comprise selecting a pre-trained style transfer network, trained by a style transfer network training system, such as style transfer network training system 100, according to one or more operations of method 400. In particular, the trained style transfer network selected at operation 308 comprises a style transfer network trained using a clinical quality loss based on the one or more clinical quality metrics selected at operation 306, and a similarity loss based on a visual difference between style transferred medical images produced by the style transfer network, and medical images of the target style (wherein the target style is the same target style selected at operation 304). Further, the trained style transfer network may include one or more pieces of metadata, indicating one or more training parameters, such as a clinical quality estimator used during training, a clinical quality metric evaluated by the clinical quality estimator, a target style domain to which the style transfer network learned a mapping, and a first style domain and/or a first style for which the trained style transfer network has learned a mapping, etc. Therefore, operation 308 may comprise the image processing device selecting a trained style transfer network, based on one or more pieces of metadata associated with the style transfer network indicating the style transfer network was trained using a clinical quality loss and style loss matching the clinical quality metric selection and the target style selection.

At operation 310, the image processing device maps the medical image to a style transferred medical image using the trained style transfer network. Operation 310 may include inputting data from the medical image into the trained style transfer network. The trained style transfer network may automatically identify composing appearance characteristics of the input medical image data, and may project the identified appearance characteristics to the target style domain. As a non-limiting example, the trained style transfer network may receive a medical image having features of a first shape, brightness, color, and texture, and the style transfer network may identify the features and map the identified features to corresponding features in a target style domain, wherein, as an example, the corresponding features in the target style domain may comprise a similar or the same shape, a different brightness, a different texture, and a different color. In some embodiments, the trained style transfer network may comprise a deep neural network, and operation 310 may include inputting the one or more medical images in the first style into an input layer of the trained deep neural network. The trained deep neural network may comprise one or more convolutional layers, comprising learned filters, which may identify appearance characteristics/features of the input medical image.

Turning briefly to FIG. 5, one example of an input medical image 502, in a first style, being mapped to a style transferred medical image 504, in a target style, by a trained style transfer network 506, is shown. Input medical image 502 may comprise a medical image acquired by a first medical imaging system. Images acquired by the first medical imaging system may not meet a clinician's image appearance preferences, and in response, the clinician may employ a method, such as method 300, to map the input medical image 502 to a style transferred medical image 504, wherein the style transferred medical image 504 comprises the image appearance preferences of the clinician (that is, the appearance characteristics of the style transferred medical image 504 match a target style defining the preferred image appearance characteristics of the clinician). Both input medical image 502 and style transferred medical image 504 comprise substantially the same anatomical content, and are of the same anatomical region of a same patient, however, the input medical image 502 and the style transferred medical image 504 comprise different appearance characteristics (that is, different style). Trained style transfer network 506, may have been selected based on a clinician's target style selection and clinical quality metric selection, as described above with reference to operation 304 and operation 306. Trained style transfer network 506 comprises a learned map from the first style domain (that is, the set of appearance characteristics of the input medical image 502) to a target style domain (that is, the set of appearance characteristics of the style transferred medical image 504).

Returning to FIG. 3, at operation 312, the image processing device optionally determines a clinical quality score for the style transferred medical image. In some embodiments, determining a clinical quality score for the style transferred medical images may comprise inputting both the style transferred medical image, and the input medical image, into a clinical quality estimator, wherein the clinical quality estimator comprises one or more differentiable functions, and wherein the clinical quality estimator evaluates a difference in the selected clinical quality metric between the input medical image and the style transferred medical image. Therefore, the clinical quality score indicates a difference in clinical quality between the input medical image, and the corresponding style transferred medical image.

At operation 314, the medical imaging system optionally determines a similarity score for the style transferred medical images. In some embodiments, operation 314 comprises selecting a similarity estimator based on the target style selection of operation 304, and determining a degree of similarity between the style transferred medical image(s) produced at operation 310, and images of the target style. In some embodiments, the style similarity estimator may comprise a discriminator network, trained to determine a probability of an input image belonging to a selected class (wherein the selected class comprises images of the target style). The style transferred medical image may be input into the discriminator network, and a probability of the style transferred medical image belonging to the selected class may be output. In some embodiments, the output probability may be used as the similarity score.

At operation 316, the medical imaging system displays the style transferred medical image via a display device. In some embodiments, operation 316 may comprise displaying the style transferred medical image produced at operation 310, via a display device, such as display device 220. In some embodiments, method 300 may optionally include operation 318, wherein the medical imaging system displays the similarity score and/or the clinical quality score via the display device. In some embodiments, the clinical quality score and/or the similarity score may be stored as meta data associated with the style transferred medical image. In one embodiment, the clinical quality score and or the similarity score may be stored in a DICOM header of the style transferred medical image.

Following operation 318, method 300 may end. Method 300 may enable a clinician to select a preferred target style, and one or more clinical quality metrics pertaining to a current clinical task (e.g., detection of lesions, evaluation of vasculature, detection of bone fractures, etc.), and a trained style transfer network may be selected based on the selected target style and clinical quality metrics. The trained style transfer network may comprise a learned mapping between appearance characteristics of the first style domain and corresponding appearance characteristics of the target style domain. The mapping may further have been learned under a constraint to maintain the selected clinical quality metric of the input medical images, and output style transferred medical images within a pre-determined threshold of each other. This may enable a clinician to evaluate/diagnose medical images in a preferred style, without the need for the clinician to manually edit the medical images.

Further, by determining clinical quality scores and similarity scores for the style transferred medical images, and by displaying the clinical quality score and/or similarity score (or by making these clinical quality and similarity scores available for viewing by a clinician), a clinician may be informed regarding changes in clinical quality that may have occurred during the mapping from the first style to the target style. Thus, a clinician may make the final determination in deciding whether or not to use style transferred medical images to perform a diagnosis.

Turning to FIG. 4, an example of a training method 400, which may be executed by one or more of the systems described above, is shown. In one embodiment, method 400 may be used to train a style transfer network, such as style transfer network 106, shown in FIG. 1, to map medical images from a first style domain to a target style domain, while preserving the anatomical content and one or more clinical quality metrics of the medical images.

Method 400 begins at operation 402, where the image processing device selects a set of medical images in a first style, and a set of target images in a target style. The target images differ in at least one appearance characteristic with respect to the medical images. In some embodiments, appearance characteristics comprise features such as brightness, color, contrast, shading, texture, etc. The number of target images and the number of medical images may be different or equal, but need not necessarily belong to a same patient, or include a same anatomical region. Further, the target images and the medical images are not paired or labeled, such as in conventional supervised training. The target images and medical images may comprise medical images from different patients, may comprise different anatomical regions, may be different in number, and may be unlabeled.

At operation 404, the image processing device selects a clinical quality estimator. In some embodiments, the clinical quality estimator may comprise a deep convolutional neural network, trained to identify one or more clinically relevant features in an input image, and to produce a score indicating one or more attributes of the identified clinically relevant feature. In some embodiments, the clinical quality estimator may comprise a pre-trained deep neural network or a model observer to produce a lesion detectability score for input medical images.

At operation 406, the image processing device selects a style similarity estimator. The style similarity estimator may comprise one or more differentiable functions, configured to receive style transferred medical images as input, and output a similarity score/similarity loss, indicating the similarity in appearance between the style transferred medical images and the target images. In some embodiments, the style similarity estimator may comprise a discriminator network. In some embodiments, the style similarity estimator may comprise a siamese neural network. In some embodiments, the style similarity estimator is configured to output a probability of an input image belonging to the set of target images.

At operation 407, the image processing device selects an image content regularizer. The image content regularizer may comprise one or more differentiable functions, which take medical images and style transferred medical images as input, and produce a content loss as output. The image content regularizer may be configured such that as the difference in anatomical content between an input medical image, and an output style transferred image increases, the content loss also increases. Image content regularizer may be configured to compute pixelwise distances between medical images and style transferred medical images, wherein the content loss may be based on the summed or averaged pixelwise distances. The distance metric used in the image content regularizer may be, but are not limited to the L1 or the L2 distance. The image content regularizer helps tether the overall content, as opposed to the style, of style transferred medical images, to the content of medical images.

At operation 408, the image processing device optionally trains the style similarity estimator using the set of target images. In some embodiments, operation 408 includes training the similarity estimator to identify features present in images belonging to the set of target images, and to use the identified features to distinguish/discriminate between images belonging to the set of target images and images belonging to other sets. In some embodiments, style similarity estimator may be pre-trained. In some embodiments, style similarity estimator may be trained at the same time during the training of the style transfer network.

At operation 410, the image processing device generates a set of style transferred medical images from the set of medical images using a style transfer network. Operation 410 may include inputting data from the set of medical images into the un-trained style transfer network. The un-trained style transfer network may automatically identify composing appearance characteristics of the input medical image data, and may project the identified appearance characteristics to the target style domain using the initialized/untrained weights. In some embodiments, the un-trained style transfer network may comprise a deep neural network, and operation 410 may include inputting the set of medical images in the first style into an input layer of the un-trained deep neural network.

At operation 412, the image processing device determines a clinical quality loss by comparing the set of style transferred medical images to the set of medical images using the clinical quality estimator. The clinical quality loss represents a difference in clinical quality for one or more clinical quality metrics, between the medical images and the corresponding style transferred medical images. As the difference in clinical quality between an input medical image, and a corresponding style transferred medical image produced by the style transfer network increases, the clinical quality loss also increases. In one embodiment, the clinical quality loss may comprise an absolute value of a difference in a clinical quality metric determined for an input medical image and a same clinical quality metric determined for a corresponding style transferred medical image produced by the style transfer network.

At operation 413, the image processing device determines a content loss of the style transferred medical images using an image content regularizer. The image content regularizer may be configured such that as the difference in overall anatomical content between an input medical image, and an output style transferred image increases, the content loss also increases. Image content regularizer may be configured to compute pixelwise differences between medical images and style transferred medical images, wherein content loss may be based on the summed pixelwise differences.

At operation 414, the image processing device determines a similarity loss for the style transferred medical images using the style similarity estimator. The similarity loss represents a quantification of the differences in appearance between style transferred medical images and target images. In other words, the style similarity estimator evaluates the visual characteristics of the style transferred medical images, and compares this with the visual characteristics of the target images, to produce a numerical value indicating a degree of stylistic similarity between the target images and style transferred medical images.

At operation 416, the image processing device aggregates the clinical quality loss, the content loss, and the similarity loss, to produce a cumulative loss. The similarity loss, the content loss, and the clinical quality loss, may be aggregated to form a cumulative loss, wherein the cumulative loss may comprise a weighted sum or weighted average of the similarity loss, the content loss, and the clinical quality loss. In some embodiments, each of the similarity loss, the content loss, and the clinical quality loss, may have an associated weight (that is, three distinct weights may be used to determine the cumulative loss, one for each of the above said loss terms), and the cumulative loss may be determined by multiplying each of similarity loss, the content loss, and the clinical quality loss by its associated weight, and summing the products so obtained. In some embodiments, the weights used to determine the cumulative loss may be manually set. In some embodiments, the weights used to determine the cumulative loss may be learned via automatic hyper-parameter search. In one embodiment, the weights used to determine the cumulative loss may be determined using Bayesian optimization or reinforcement learning.

At operation 418, the image processing device updates style transfer network parameters by minimizing the cumulative loss. In some embodiments, updating the style transfer network parameters includes adjusting parameters of the one or more style transfer networks by backpropagating the cumulative loss through the layers of the style transfer network using a backpropagation algorithm. In one embodiment, operation 418 comprises the image processing device adjusting the weights and biases of the layers of the style transfer network based on the cumulative loss determined at operation 416. In some embodiments, back propagation of the cumulative loss may occur according to a gradient descent algorithm, wherein a gradient of the cumulative loss function (a first derivative, or approximation of the first derivative) is determined for each weight and bias of the style transfer network. Each weight (and bias) of the style transfer network is then updated by adding the negative of the product of the gradient of the cumulative loss, determined with respect to the weight (or bias) and a predetermined step size, according to the below equation:

$$P_{i+1} = P_i - \eta \frac{\partial \text{Loss}}{\partial P_i}$$

where $P_{i+1}$ is the updated parameter value, $P_i$ is the previous parameter value, $\eta$ is the step size, and $$\frac{\partial \text{Loss}}{\partial P_i}$$

is the partial derivative of the cumulative loss with respect to the previous parameter.

Following operation 418, method 400 may end. It will be appreciated that method 400 may be repeated until one or more conditions are met. In some embodiments, the one or more conditions may include the weights and biases of the transfer network converging (that is, a rate of change of the parameters decreases to below a pre-determined threshold rate of change), the cumulative loss determined at operation 416 decreasing to below a pre-determined, non-zero, threshold (in some embodiments, the cumulative loss may be determined using a validation dataset, distinct from the training dataset). In this way, method 400 enables a deep neural network to learn a mapping from a first style domain to a target style domain, wherein the mapping preserves the anatomical content and a clinical quality, as determined by the clinical quality estimator, of the medical images, thereby preventing degradation of clinical quality upon mapping of the input medical images to the style transferred medical images.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
   acquiring a medical image of an anatomical region of a subject, wherein the medical image is in a first style;
   selecting a target style, wherein the target style is distinct from the first style;
   selecting a clinical quality metric, wherein the clinical quality metric corresponds to a current diagnostic purpose for acquiring the medical image, and wherein the clinical quality metric comprises one or more of a lesion detectability index from a model observer, and a cancer classification score from a pre-trained classifier;
   selecting a trained style transfer network based on the target style and the clinical quality metric;
   mapping the medical image to a style transferred medical image using the trained style transfer network while maintaining the clinical quality metric of the medical image in the style transferred medical image, wherein the style transferred medical image is in the target style; and
   displaying the style transferred medical image via a display device.

2. The method of claim 1, wherein the first style corresponds to a first imaging modality, and wherein the target style corresponds to a second imaging modality, wherein the first imaging modality and second imaging modality are distinct, and wherein the trained style transfer network comprises a learned map from medical images of the first imaging modality to medical images of the second imaging modality.

3. The method of claim 1, wherein the first style corresponds to a first imaging device of a first imaging modality, the second imaging style corresponds to a second imaging device of the first imaging modality, wherein the first imaging device and the second imaging device are distinct, and wherein the trained style transfer network comprises a learned map from medical images of the first imaging device of the first imaging modality to medical images of the second imaging device of the first imaging modality.

4. The method of claim 1, wherein selecting the clinical quality metric comprises selecting the clinical quality metric based on the anatomical region of the subject.

5. The method of claim 1, wherein mapping the medical image to the style transferred medical image using the trained style transfer network comprises prioritizing preservation of anatomical features in a highlighted region of the medical image.

6. The method of claim 1, the method further comprising:
   determining a similarity score for the style transferred medical image using a style similarity estimator, wherein the style similarity estimator was used to train the trained style transfer network; and
   displaying the similarity score via the display device; or
   storing the similarity score in meta-data of the style transferred medical image.

7. The method of claim 1, the method further comprising:
   determining a clinical quality score for the style transferred medical image by comparing the style transferred medical image with the medical image using a clinical quality estimator, wherein the clinical quality estimator was used to train the trained style transfer network; and
   displaying the clinical quality score via the display device; or
   storing the clinical quality score in meta-data of the style transferred medical image.

8. An image processing system comprising:
   a display device;
   a user input device;
   a memory storing a trained style transfer network and instructions; and a processor communicably coupled to the display device, the user input device, and the memory, and when executing the instructions, configured to:
  receive a medical image of an anatomical region of a subject, wherein the medical image is in a first style;
  receive a target style selection via the user input device, wherein the target style selection indicates a target style;
  receive a clinical quality metric selection via the user input device, wherein the clinical quality metric selection indicates a clinical quality metric, wherein the clinical quality metric corresponds to a current diagnostic purpose for acquiring the medical image, and wherein the clinical quality metric comprises one or more of a lesion detectability index from a model observer, and a cancer classification score from a pre-trained classifier;
  select a trained style transfer network based on the target style and the clinical quality metric;
  map the medical image to a style transferred medical image using the trained style transfer network while maintaining the clinical quality metric of the medical image in the style transferred medical image, wherein the style transferred medical image is in the target style; and
  display the style transferred medical image via the display device.

9. The image processing system of claim 8, wherein the first style corresponds to a first imaging modality, and wherein the target style corresponds to a second imaging modality, wherein the first imaging modality and second imaging modality are distinct, and wherein the trained style transfer network comprises a learned map from medical images of the first imaging modality to medical images of the second imaging modality.

10. The image processing system of claim 8, wherein the first style corresponds to a first set of medical images, and wherein the target style corresponds to a second set of clinician adjusted medical images, wherein the trained style transfer network comprises a learned map from a first set of appearance characteristics of the first set of medical images to a second set of appearance characteristics of the second set of clinician adjusted medical images.

11. The image processing system of claim 8, wherein, when executing the instructions, the processor is further configured to:
  determine a similarity score for the style transferred medical image using a style similarity estimator, wherein the style similarity estimator comprises a trained deep neural network stored in the memory; and
  display the similarity score via the display device.

12. The image processing system of claim 8, wherein, when executing the instructions, the processor is further configured to:
  determine a clinical quality score for the style transferred medical image by comparing the style transferred medical image against the medical image using a clinical quality estimator, wherein the clinical quality estimator comprises a trained deep neural network stored in the memory; and
  display the clinical quality score via the display device.

13. The method of claim 1, wherein the clinical quality metric comprises a lesion detectability index from a model observer.

14. The method of claim 1, wherein the clinical quality metric comprises a cancer classification score from a pre-trained classifier.

15. The method of claim 1, wherein the current diagnostic purpose comprises detecting lesions.

16. The method of claim 1, wherein the current diagnostic purpose comprises detecting bone fractures.

17. The method of claim 1, wherein the current diagnostic purpose comprises evaluating vasculature.

18. The method of claim 1, wherein the current diagnostic purpose comprises detecting lesions and the clinical quality metric comprises a lesion detectability index from a model observer.

19. A method comprising:
  acquiring a medical image of an anatomical region of a subject, wherein the medical image is in a first style;
  selecting a target style, wherein the target style is distinct from the first style;
  selecting a clinical quality metric, wherein the clinical quality metric corresponds to a current diagnostic purpose for acquiring the medical image, and wherein the current diagnostic purpose comprises one or more of detecting lesions, detecting bone fractures, and evaluating vasculature;
  selecting a trained style transfer network based on the target style and the clinical quality metric;
  mapping the medical image to a style transferred medical image using the trained style transfer network while maintaining the clinical quality metric of the medical image in the style transferred medical image, wherein the style transferred medical image is in the target style; and
  displaying the style transferred medical image via a display device.

20. An image processing system comprising:
  a display device;
  a user input device;
  a memory storing a trained style transfer network and instructions; and
  a processor communicably coupled to the display device, the user input device, and the memory, and when executing the instructions, configured to:
    receive a medical image of an anatomical region of a subject, wherein the medical image is in a first style;
    receive a target style selection via the user input device, wherein the target style selection indicates a target style;
    receive a clinical quality metric selection via the user input device, wherein the clinical quality metric selection indicates a clinical quality metric, wherein the clinical quality metric corresponds to a current diagnostic purpose for acquiring the medical image, and wherein the current diagnostic purpose comprises one or more of detecting lesions, detecting bone fractures, and evaluating vasculature;
    select a trained style transfer network based on the target style and the clinical quality metric;
    map the medical image to a style transferred medical image using the trained style transfer network while maintaining the clinical quality metric of the medical image in the style transferred medical image, wherein the style transferred medical image is in the target style; and
    display the style transferred medical image via the display device.

* * * * *